US012560367B2

(12) United States Patent
Van Halsema

(10) Patent No.: US 12,560,367 B2
(45) Date of Patent: Feb. 24, 2026

(54) MEASURING SYSTEM FOR FOODSTUFFS

(71) Applicant: LANVI PATENT B.V., Maassluis (NL)

(72) Inventor: Frans Emo Diderik Van Halsema, Maassluis (NL)

(73) Assignee: LANVI PATENT B.V., Maassluis (NL)

( * ) Notice: Subject to any disclaimer, the term of this patent is extended or adjusted under 35 U.S.C. 154(b) by 297 days.

(21) Appl. No.: 17/765,686

(22) PCT Filed: Sep. 25, 2020

(86) PCT No.: PCT/NL2020/050595
§ 371 (c)(1),
(2) Date: Mar. 31, 2022

(87) PCT Pub. No.: WO2021/066645
PCT Pub. Date: Apr. 8, 2021

(65) Prior Publication Data
US 2022/0364780 A1 Nov. 17, 2022

(30) Foreign Application Priority Data
Oct. 1, 2019 (NL) ..................................... 2023924

(51) Int. Cl.
*G01N 11/12* (2006.01)
*A23B 2/00* (2025.01)
(Continued)

(52) U.S. Cl.
CPC ............ *F25D 11/006* (2013.01); *A23B 2/001* (2025.01); *A23B 2/003* (2025.01); *A23B 2/30* (2025.01);
(Continued)

(58) Field of Classification Search
None
See application file for complete search history.

(56) References Cited

U.S. PATENT DOCUMENTS

| | | | |
|---|---|---|---|
| 10,605,674 B1 * | 3/2020 | Holbrook | ................. G01K 3/00 |
| 2008/0003649 A1 * | 1/2008 | Maltezos | ............ B01L 3/50851 |
| | | | 435/286.1 |

(Continued)

FOREIGN PATENT DOCUMENTS

KR 102328512 B1 * 11/2021 ............. G06Q 10/04

OTHER PUBLICATIONS

International Search Report mailed on Feb. 9, 2021 in PCT/NL2020/050595 filed on Sep. 25, 2020 (total 4 pages).

(Continued)

*Primary Examiner* — Uzma Alam
*Assistant Examiner* — Chad Andrew Reverman
(74) *Attorney, Agent, or Firm* — Oblon, McClelland, Maier & Neustadt, L.L.P.

(57) ABSTRACT

A measuring system for automatically determining and/or monitoring the quality of a liquid or viscous foodstuff, including a housing with an interior space for a product container for the foodstuff, the product container has a product space for the foodstuff and a lid provided with a probe with a thermometer, a heating and cooling device for the interior space, a sensor device for determining a non-temperature quality-related parameter value of the foodstuff, and a control unit designed to control the measuring system, measure, store, process and/or export the measured parameter values, and to control the heating and/or the cooling system according to a desired time-temperature program. The cooling system includes a cold buffer, a cooler for the cold buffer, and a separate refrigerant circuit. The cold buffer includes a buffer holder with a phase-transition material, wherein the refrigerant circuit includes a cooling circuit with a pump.

21 Claims, 1 Drawing Sheet

(51) Int. Cl.

| | |
|---|---|
| *A23B 2/30* | (2025.01) |
| *A23B 2/80* | (2025.01) |
| *A23B 11/123* | (2025.01) |
| *A23B 11/145* | (2025.01) |
| *F25D 11/00* | (2006.01) |
| *F25D 29/00* | (2006.01) |
| *F28D 20/02* | (2006.01) |
| *G01N 21/17* | (2006.01) |
| *G01N 21/84* | (2006.01) |
| *G01N 27/04* | (2006.01) |
| *G01N 33/02* | (2006.01) |
| *F25B 29/00* | (2006.01) |

(52) U.S. Cl.
CPC .......... *A23B 2/8055* (2025.01); *A23B 11/123* (2025.01); *A23B 11/145* (2025.01); *F25D 29/00* (2013.01); *F28D 20/023* (2013.01); *G01N 11/12* (2013.01); *G01N 21/84* (2013.01); *G01N 27/04* (2013.01); *G01N 33/02* (2013.01); *A23V 2002/00* (2013.01); *F25B 29/00* (2013.01); *G01N 2021/1789* (2013.01)

(56) References Cited

U.S. PATENT DOCUMENTS

| | | | | |
|---|---|---|---|---|
| 2014/0326591 A1* | 11/2014 | Harman | ................. | B01D 3/106 202/184 |
| 2015/0143831 A1* | 5/2015 | Chou | .................... | F25D 11/025 62/190 |
| 2017/0100495 A1* | 4/2017 | Shur | ...................... | H04N 7/183 |
| 2024/0336699 A1* | 10/2024 | Ang | ................... | C07K 14/5443 |

OTHER PUBLICATIONS

NL Search Report dated Jun. 23, 2020 in Application NL 2023924 filed on Oct. 1, 2019 (with Translation of Categories, total 3 pages).

* cited by examiner

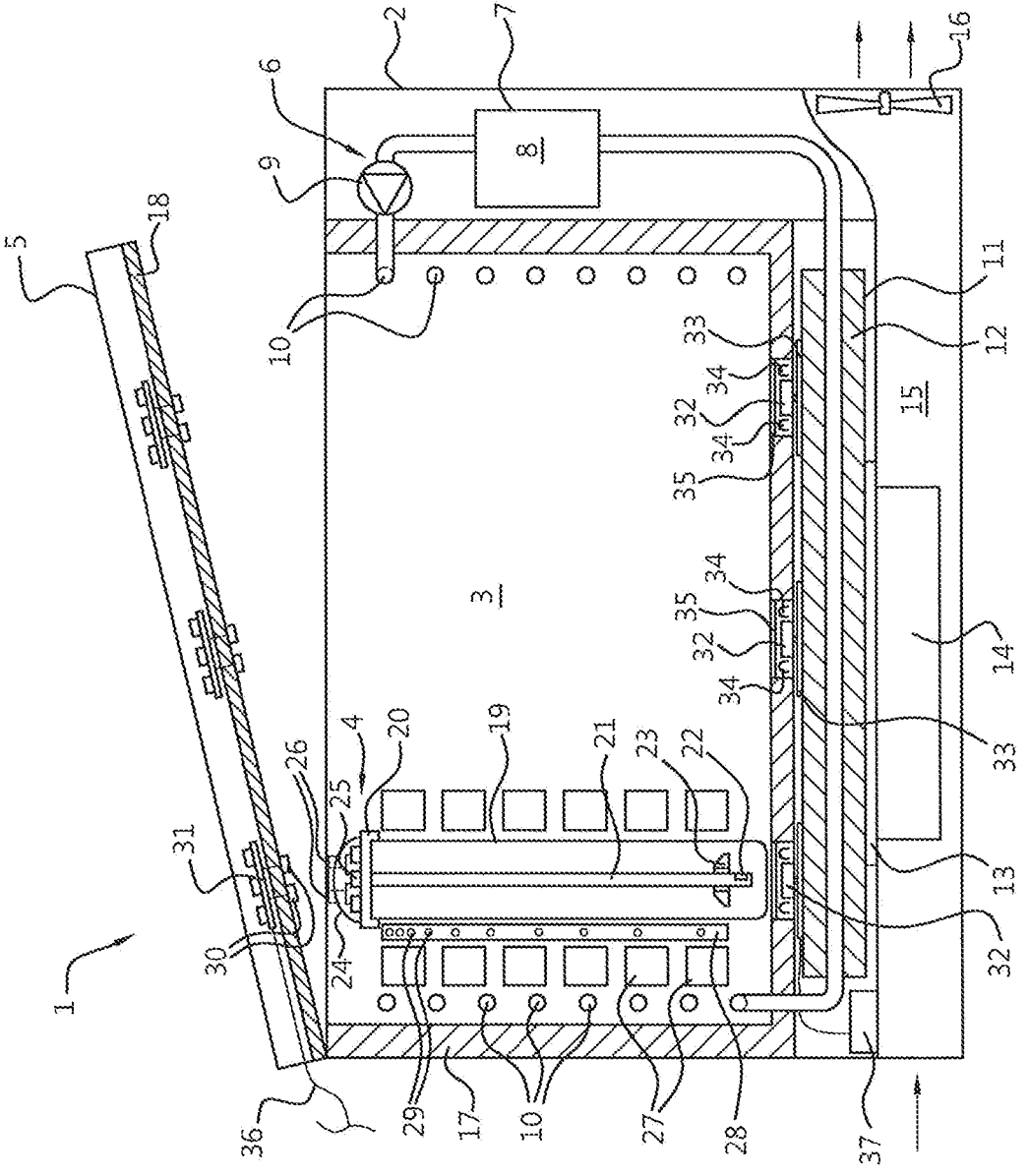

MEASURING SYSTEM FOR FOODSTUFFS

The present invention relates to a measuring system for determining and/or monitoring the quality of a liquid or viscous foodstuff, and comprising a housing with an interior space for at least one product container for such a foodstuff, a product container with a product space for the foodstuff, and with a lid and a thermometer, a heating and cooling device for cooling and/or heating the interior space, a sensor device for determining a quality-related parameter value of said foodstuff, not being the temperature, and a control unit which is operatively connected to the heating and cooling to device, the sensor device and the thermometer, and is configured to control the measuring system, and to control the heating and/or the cooling system according to a desired time-temperature program for the interior space.

Such measuring systems are known per se. They serve inter alia to measure quality properties of foodstuffs, such as in particular shelf life/decay and stability.

A drawback of the known devices is that these often operate in a complicated way and may also deliver unreliable results, because people operate and read the devices. However, especially with foodstuffs, it is important that the measurements are reliable. This requires many measurements for statistically reliable results and circumstances which are readily controllable, and also requires a large number of measured values to be read. Nowadays, there is furthermore a shift away from the consumption of products containing animal proteins to products with vegetable proteins, and to products containing (much) less salt and/or fat. This requires a change in recipe for a very large number of (existing and new) products, with associated changes in properties.

A very important property with foodstuffs is the shelf life/stability. This may depend to a large degree on the temperature and the time. Consequently, still more measurements are required, in particular with measurements which have to simulate use in practice with its many changes in temperature, and thus a still greater risk of errors.

It is an object of the present invention to provide a suitable measuring system of the kind described in the introduction which is very flexible during use, reduces the risk of errors and is suitable to automatically measure and/or monitor product properties of foodstuffs.

The invention achieves this object with a measuring system as claimed in claim 1, in particular a measuring system for automatically determining and/or monitoring the quality of a liquid or viscous foodstuff, and comprising a housing with an interior space for at least one product container for such a foodstuff, a product container with a product space for the foodstuff, and with a lid provided with a probe with a thermometer which projects into the product space, a heating and cooling device for cooling and/or heating the interior space, a sensor device for determining a quality-related parameter value of said foodstuff, not being the temperature, and a control unit which is operatively connected to the heating and cooling device, the thermometer, and the sensor device, and is configured to control the measuring system, to repeatedly measure the parameter value by means of the sensor device, to store, process and/or export the measured parameter values, and to control the heating and/or the cooling system according to a desired time-temperature program for the interior space, wherein the cooling system comprises a cold buffer, a cooler for the cold buffer, and a separate refrigerant circuit, wherein the cold buffer comprises a buffer holder with a phase-transition material (PCM), wherein the refrigerant circuit comprises a closed-circuit line which is filled with a liquid refrigerant and is in heat-exchanging contact with the interior space and with the cold buffer, as well as a pump for pumping the refrigerant around.

By means of the system according to the present invention, it is possible to automatically perform various measurements on a foodstuff which, in addition, may be performed as a function of the time and of the temperature. Furthermore, the controlled heating and cooling system is able to simulate practical situations, such as cooled production and transportation, subsequently transfer onto a non-refrigerated platform, refrigerated distribution, non-refrigerated transportation from a truck to the cooling system in a shop, non-refrigerated transportation to a home, refrigerated storage in a refrigerator, use outside the cooling system on cool or hot days, etc. For all such situations, it is necessary to know how the foodstuff will behave and in particular what the shelf life is under such circumstances. The latter can be determined accurately and in particular easily, repeatedly and automatically and practically faultlessly with the measuring system according to the invention. It is not necessary to remove a product container from the thermostration chamber each time in order to perform a measurement, so that it is even possible to measure continuously, thus making it possible to monitor without the circumstances, such as temperature, being disrupted in the interim by removing the foodstuff from the interior space and performing a measurement.

It is also important that the foodstuff, at least the interior space containing the product container with the foodstuff, can be refrigerated quickly. The reason for this is that the quickest changes occur at the relatively high temperatures, but in order to be able to accurately determine the time and temperature dependency, it is desirable to stop changes as much as possible, in particular if the foodstuff contains proteins or the like, after a certain set temperature profile. To this end, the temperature has to be lowered quickly at the end of the profile. This can be achieved by means of the active cooling system in the system according to the invention, and that automatically, without human intervention.

In the present invention, the expression "a liquid or viscous foodstuff" is understood to mean "any product destined for human or animal consumption with a viscosity which is such that this product is deformable on account of the force of gravity and without a substantial change in volume either assumes the shape of the container or is pumpable as a substantially single mass". This comprises ready-made products, such as dairy products, soups, sauces, etc., but also ingredients thereof, such as water-oil emulsions for sauces and the like.

Specific embodiments are described in the dependent claims and in the following part of the introduction to the description.

The design of the cooler is not particularly limited and may, for examples comprise a common compression heat pump, as used in a domestic refrigerator, or a Joule-Thomson cooling system. However, in important embodiments, said cooler comprises a Peltier heat pump which is configured to cool the buffer holder with phase-transition material. Such a Peltier heat pump has the advantages that it does not contain any moving parts and, in addition, is very compact, which is an advantage in particular in laboratories, where space is scarce. A drawback is the fact that the power of a Peltier heat pump is often relatively low. However, this does not have to be a problem with the present invention, as the cooling system is used to cool the buffer, which may also take place in a period in which the interior space is actually kept at a high temperature. During this entire time, the Peltier heat pump can cool the buffer, at least extract heat therefrom, so that even a low power output can result in a large buffer. Incidentally, in practice, a fan and also a heatsink are provided in order to dissipate the absorbed heat from the system. Another drawback is the fact that a Peltier cooler often does not tolerate high temperatures, such as in excess of 80° C., but this is not a problem in this case due to the limitation to cooling. Heating can be provided by a separate heating system, such as electrical resistance wires or the like. Incidentally, it is not necessary to use a phase change material as cold buffer, but since a PCM has an even greater heat capacity than water due to absorbing latent heat, the measuring system may be made even more compact. In addition, the temperature can be defined very well as, for example, the temperature of the phase transition of the PCM. Such a temperature can be chosen from the available PCMs, and may be in a range from −50 to +150° C., with temperatures between −10 and +6° C. being particularly relevant for use with foodstuffs. In itself, ice/water is a very well-known and widely usable PCM, but it has the drawback that it expands relatively significantly during freezing, which is undesirable from a structural engineering point of view, as it may lead to bursting, or to the formation of insulating air gaps (during melting). In addition, the ice-water transition is not suitable for temperatures over 0° C. This is the reason why, for example, organic PCMs or crystals with a solid-solid phase transition may offer advantages here, such as wide availability on the market.

In embodiments, the time-temperature program comprises the control unit bringing the interior space to an, optionally time-dependent, temperature by means of the heating and cooling device during a desired time period. This is the simplest use of the measuring system according to the invention, in which the measuring system itself sets the temperature and performs the measurements. It is also possible to simulate real life by subjecting the foodstuff to cycles of warming up and cooling down by controlling the heating and cooling device in a targeted manner. Obviously, use is made in this case of the thermometer to control the temperature. In addition, it is possible to use any desired time-temperature profile by inputting the desired one or more temperatures and the associated time periods and/or number of repetitions in the control unit using an input apparatus which is suitable for and has been provided for the purpose. The measuring system according to the invention subsequently executes the time-temperature profile and performs the required measurements in the process.

In order to cool down the container, the control unit is, in particular, configured to control the pump in order to make the refrigerant flow past the buffer holder and subsequently past or through the interior space with the product container. By means of such a forced cooling system, undesired further changes in the foodstuff can effectively be prevented. In this case, making the refrigerant flow through the interior space, that is to say directly past the product containers, may cool even more effectively.

In embodiments, the buffer holder comprises a heat-conducting foam which is at least partly filled with the phase change material. In many cases, the PCMs are able to store or to deliver a large amount of heat, but they are bad heat conductors, so that the speed of delivery/absorption is relatively low. In order to counter this, it is advantageous if the PCM is provided in a metal foam or lattice or the like, so that the latter is able to absorb the heat from or emit the heat to the PCM locally and across a much larger surface and to subsequently convey the heat internally to the outside world, such as a cooling liquid. In particular, the heat-conducting foam is a metal foam, such as aluminium foam, which has excellent heat conductivity.

Advantageously, the phase change material has a phase transition temperature below 0° C. Thus, it is possible to cool quickly and by a significant amount. However, other temperatures are certainly possible, for example just above zero, if freezing is to be avoided at all costs. The cold buffer may be filled in a corresponding manner.

By means of the sensor device, measurements are performed on the foodstuff in order to determine relevant parameter values, for example, for absolute or relative product properties or for more general properties, such as shelf life. In embodiments, the sensor device comprises at least one of the following: a camera which is advantageously placed under the product container and directed upwards towards the product container, wherein the product container is at least partly transparent or open, and/or a viscosity-measuring device for measuring a viscosity of said foodstuff, and/or a measuring device for conductivity or other electrical properties of said foodstuff, and/or an optical measuring device for measuring a transmission, a diffusion and/or a reflection value of said foodstuff.

By means of the camera, it is possible to collect a very large amount of information, such as a color and/or transparency, as well as changes therein, and also whether, for example, deposits or other visible physicochemical changes occur in the foodstuff. To this end, the camera is optionally provided with image-processing software. In addition, a source of light is advantageously provided, such as one or more LEDs which may be provided around the camera or on the probe and thus, in use, in the foodstuff. Thus, reflection, transmission and/or diffusion measurements may be performed on the foodstuff. Obviously, in this case, the product container is at least partly optically transparent, such as made in its entirety from glass, a plastic, such as polycarbonate, etc., or also provided with an optically transparent window at the location of the camera.

Alternatively or additionally, the sensor device comprises a viscosity-measuring device for measuring a viscosity of said foodstuff. The "falling ball meter", for example, which is known per se is suitable for this purpose, as is any other known viscometer. Viscosity is a property of foodstuffs which is important to consumers, in particular in the case of dairy products, which may depend greatly on temperature, mechanical load, etc. The viscosity may be measured by the sensor device at any moment during heating or cooling, so that even virtually continuous measurements are possible.

Additionally or alternatively, the sensor device comprises a measuring device for conductivity or other electrical properties of said foodstuff. For example, a direct conductivity meter may provide an indication for deposits developing which often develop from dissolved salts. When salts which were originally dissolved are deposited, it is possible that the conductivity decreases. One important other electrical measuring device is an electrochemical impedance spectroscope (EIS) which records a (complex) impedance spectrum of the foodstuff by applying a spectrum of voltages over a plurality of electrodes. This spectrum, i.e. the complex and real parts of the impedance as a function of the frequency of the voltage used, provides a fingerprint of, at least a large amount of information about, the composition of the foodstuff and thus also about changes therein. In addition to a plurality of electrodes, such an EIS preferably comprises two electrical sources and two measuring electrodes, also a sweep voltage generator and a signal sensor and processor.

Alternatively or additionally, the sensor device comprises an optical measuring device for measuring a transmission, a diffusion and/or a reflection value of said foodstuff. In addition or instead of a camera, it is also possible to provide such an optical measuring device. In particular, such an optical measuring device is provided in the product space, in particular on, along or at the probe. Advantageously, the optical measuring device comprises one or more light conductors, such as optical fibers, as well as a source of light, with one or more LEDs or the like, as well as one or more optical sensors. In this case, the light of the light source is injected in the foodstuff via the light conductors. There, it is reflected, passes through or is diffused, following which one or more light conductors inject this light which has been influenced by the foodstuff and pass it to the optical sensor(s). Thus, it is also possible, in addition to the camera, to perform sensible measurements, even with optically very dense foodstuffs, such as dairy products, since the light conductors and their respective injection surfaces can be placed much closer together than the camera.

In particular, it is also advantageous if the sensor device(s) is/are incorporated in the respective lid of the product container. Thus, it is even possible, in principle, to perform different measurement on one and the same product by changing the lid for a lid with another sensor device.

Advantageously, the sensor device(s) is/are replaceably tillable, such as in the lid of the product container. This means that either the sensor device is fittable in and removable from the lid, or that the lid is replaceable in its entirety, including the sensor device or the probe. An important advantage thereof is that it is very simple to fit the required sensor device(s) for each experiment and for each product in the system, and to automatically perform the associated measurements. This provides a high degree of flexibility.

In embodiments, the measuring system comprises a plurality of housings, each for or provided with a container for or with a liquid or viscous foodstuff, wherein the plurality of housings are mechanically and electrically couplable to each other. Optionally, the housings are also thermally connectable to the cooling and heating device, wherein the control unit is configured to control the heating and/or the cooling system according to the same or different simultaneous desired time-temperature programs for at least two of the plurality of housings. The cooling and/or heating device may comprise various heating elements which are individually actuable by the control unit and the cooling system may differ for each housing, for example by the restrictor valves or control valves provided for the refrigerant. Every housing contains a separately closable lid, so that one or more product containers with foodstuff can be placed or removed without affecting product containers in other housings. This modular construction is advantageous if a large number of measurements have to be performed. If, in addition, the control units of the housings are coupled, at least in such a way that the measured values or other data pass from the respective control units to a receiver via a connection, a very flexible measuring system is provided which is able to perform measurements autonomously, automatically virtually continuously or continuously for relevant product properties of foodstuffs in a temperature-controlled environment.

The invention will be explained below in more detail by means of one or more exemplary embodiments and the drawing. In the latter, the sole FIGURE diagrammatically shows a sectional view of a measuring system according to the invention.

The FIGURE diagrammatically shows a sectional view of a measuring system 1 according to the invention. The measuring system 1 comprises a housing 2 with an interior space 3 and which contains one product container 4 as well as a lid 5.

Furthermore, a cooling device is denoted by reference numeral 6, which comprises a storage container 7 for refrigerant 8, a pump 9, a pipe system 10, a cold buffer 11 with a phase change material 12, a Peltier cooler 13, a heatsink 14, a ventilation space 15 and a fan 16. Insulating material 17 and 18, respectively, is provided in the housing 2 and the lid 5, respectively.

The product container 4 comprises a cup 19 and a container lid 20 with a probe 21 with a thermometer 22. A magnetic body is denoted by reference numeral 23. Furthermore, a sensor sphere 24 surrounds optical sensors 25 and is provided with contacts 26. Electromagnetic coils 27 surround a carrier 28 with sensors 29. The lid 5 is provided with countercontacts 30 to electronics 31.

Cameras 32 are connected to respective camera control units 33, Optionally, a plurality of LEDs are arranged around the camera and above them a a protective glass 35 is placed. Finally, reference numeral 36 denotes a connection to the outside and reference numeral 37 denotes a control unit for the system 1.

The illustrated system 1 comprises a housing 2 and lid 5 of, for example, metal or plastic, which surround an interior space 3 which is insulated with insulating material 17 and 18, A plurality of product containers 4 may be placed in the interior space 3, in the illustrated example three, of which only one is shown for the sake of clarity.

By means of the cooling system 6, the interior space 3 may be brought to a desired temperature by the control unit 37. It should be stressed here that the cooling system 6 is additionally provided with a heating device (not shown here), such as electrical heating wires or the like. These can bring the interior space to a higher desired temperature in a manner which is known per se. Subsequently, after some desired time period, the control unit 37 may actuate the cooling part, that is to say the cooling system 6, to bring the interior space 3 to a desired lower temperature. To this end, the cooling system 6 comprises a storage container 7 with a refrigerant 8, such as glycol, which serves to transfer heat. To this end, a pump 9 pumps the refrigerant 8 through a, for example spiral-shaped, pipe system 10 around the interior space 3. In this case, the refrigerant 8 may dissipate its heat to the phase change material (PCM) 12 in the cold buffer 11. The PCM 12 may simply be water/ice, wherein the heat absorbed from the refrigerant 8 makes ice melt to form water, but advantageously, the PCM may also be a different material. A particular drawback of water is the fact that it expands when it solidifies, and that the melting point is at 0° C., or below if additives were added. However, numerous other PCMs are available which do not have these drawbacks and which have phase transitions which are, for example, at a temperature between 5 and 40° C. For example, the interior space may be heated first to a pasteurisation temperature, such as 72° C., or also a sterilisation temperature, such as around 130° C., important other temperatures are use temperatures to which foodstuffs may be exposed, such as heating up to 30 to 40° C. on a loading platform in the sun or on the table of a consumer, and then back to a cooling temperature of 4-6° C. It is also possible to measure how the properties of the foodstuff change over time at one and the same temperature, such as 6, 8 or 10° C. In this case, it is very important that any changes can be stopped in all cases, at least be prevented as much as possible, when a certain desired temperature regime has been completed. To this end, it is important that the foodstuff can be cooled quickly to in particular a desired end temperature, such as a temperature at which no (significant) further change occurs, in particular with regard to sugars and/or bacterial growth. Therefore, an active cooling system is desired. Should the case arise, the thermometer 22 measures the temperature of the foodstuff in the product container 4, with which signal the control unit 37 can actuate the cooling system 6 and or the heating system.

For this active cooling system, a refrigerant is thus pumped around in the cooling circuit with pipe system 10 by means of the pump 9. The PCM 12 in the cold buffer 11 is itself cooled by means of any known cooling device, such as a heat pump or a Joule-Thomson cooling system. However, it is advantageous to choose a compact cooling system, because space is limited or may be expensive, in particular in a laboratory. In addition, moving parts are not always desired. For this reason, a Peltier cooling system 13 is advantageous, as it is compact and does not contain moving parts itself. However, in this case a fan 16 is provided which guides air past a heatsink 14 via a ventilation space 15, so that the heat can be dissipated from the system 1 in an efficient manner.

At the bottom of the interior space 3, in the bottom thereof, cameras 32 are arranged which have an upwardly directed image field and thus form an image of the underside of their respective product container 4. However, to this end, the latter has to be made either from a transparent material, such as glass or polycarbonate, or also be flexible, such as PE film, or have a transparent window. The associated control and/or processing electronics may be provided under the insulation 17, so that it is protected against the changing and sometimes extreme temperatures. Using the camera, it is possible to produce an image of the foodstuff in the product container 4. In particular, it is thus possible to observe changes in the color and/or deposits, which may be important to monitor and measure the quality overall, or certain product properties in particular, as a function of temperature and/or time.

Optionally, a light source is provided to support the operation of the camera 32, in this case in the form of a plurality of LEDs 34. The LEDs may emit light of the same or different colors and, as they are provided around the camera, they can use the same electronics platform. The LEDs 34 can emit light into the product in the product container 19 via the protective glass 35, which is made, for example, from borosilicate glass, fused glass or another translucent and preferably chemical-, temperature- and scratch-resistant material. Emitted light which has subsequently been reflected by the product can be detected by the camera 32 and then be analysed by the control unit 37, or can be transmitted externally for further processing via the connection 36. It is also still possible to provide still other sensors (not shown here) in addition to the camera 32, such as InGaAs or Si sensors, which offer better sensitivity in, for example, the (N)IR range than most cameras 32.

Another possibility is to provide a light source on the probe 21 or also, for example, in the lid 20 of the product container 4, There, light conductors, such as optical fibers, may be provided in the sensor sphere 24, where the emitted light may be injected, and the probe 21 may be inserted, Reflected light or diffused light can then also be collected by one or more light conductors in the probe and sent to the sensor sphere 24, where sensors 25 can measure the light in order to thus obtain additional information about color and, for example, transparency. A portion of the light will be reflected and a portion will be transmitted, so that the respective coefficients for the foodstuff can be determined by the control unit therefrom.

Furthermore, a viscosity-measuring device is also provided to measure the viscosity and changes therein of the foodstuff in the respective product container 4. The viscosity-measuring device comprises a series of coils 27 which are arranged around the product container 4, as well as a series of Hall sensors 29 on a carrier 28 and a magnetic body 23 around the probe 22. This is in itself similar to the known "falling ball" measurement. The control unit 37 energises the individual coils 27 in a suitable pattern. The magnetic body 23 is attracted by respective magnetic fields of the individual coils 27 and possible even, after polarity reversal, repelled, as a result of which it moves and moves, for example, upwards. When it has arrived in the upper part of the product container 4, for example, all coils which are still energised are switched off, after which the body 23 will start to drop. When it moves past the Hall sensors 29, these will emit a position-dependent signal which can be processed by the control unit 37 to a drop position as a function of time and thus as a measuring system for the speed, and therefrom the viscosity of the foodstuff in the product container. If the viscosity is very high, as is the case with emulsions, yoghurts, etc., then the viscosity may also be determined from the speed which the body 23 may reach on account of the fields of the coils 27. An important additional advantage of the described magnetic system is the fact that this can also be used to mix the foodstuff in the product container 4, in particular by repeatedly and/or quickly moving the magnetic body up and down. This mixing makes it possible, for example, to cancel sedimentation as much as possible, and to then measure the product properties. Consumers often do something similar with the respective product, such as "shake well before use".

In the exemplary embodiment described so far, one product container 4 is provided and illustrated in the interior space 3, In practice, associated coils 27, a carrier 28 with Hall sensors 29, a camera 32, etc., only some of which are shown here for the sake of clarity, will in each case be provided for each available location for a product container in the interior space 3, of which three are shown here. Also, different numbers of available locations may be provided, such as two, four, five, etc.

In use, one or more product containers 4 are filled with a foodstuff to be measured, for example with different recipes or also the same, for redundant measurements. Subsequently, the lid 5 of the system 1 is closed. As a result thereof, the insulation 17 and 18 around the interior space 3 with the product container(s) 4 seals. This also protects the electronics 31 against temperature variations. In addition, it is also possible to provide the sensors 25 in the sensor sphere 24 with insulation. At the same time, the countercontacts 30 in the lid make contact with the contacts 26 on the lid 20 of the product container, so that the electronics 31 can ensure control of the optional sensors 25, the thermometer 22, etc. Furthermore, it is possible to design the contacts 26 and/or the electronics of the product container situated behind them in such a way that the electronics 31, or the control unit 37 which is operatively connected thereto, is able to recognise the product container and, if desired, its contents. This further reduces the risk of errors by human operators.

Furthermore, a desired time-temperature profile is input into the control unit 37 by a user, such as via the connection 36, which may obviously also be designed as a wireless connection (Bluetooth® or the like) or a USB connection, SD card or even via the lid 5 provided on the product container 4, etc. The control unit 37 will subsequently actuate the heating and/or the cooling system 6, under the control of the temperature measured by the thermometer 22, in order to set the desired profile. At certain times, random or regular, the control unit 37 will cause the one or more sensors 22, 25, 29, 32 to perform one or more measurements. The measured data which are thus collected may be stored by the control unit for future use. They may also be sent to an external data storage or data processing facility via the connection 36. They may also be processed by the control unit 37, for example in order to monitor if one or more product parameters fall outside a desired range. In this case, examples thereof may be checking the color of the product or the transparency/deposits by means of the camera 32 or the viscosity. Should the value be outside a desired range, the control unit can emit an alarm signal, again for example via the connection 36. If desired, the remaining part of the time-temperature profile may be cancelled. Alternatively, it is possible to determine how long it took before the value moved outside the desired range for the foodstuff in the respective product container 4. This makes it possible, for example, to determine a shelf life.

The illustrated embodiment is by no means intended to be limiting for the invention, but only serves to explain it. The scope of protection of the invention is determined by the attached claims.

The invention claimed is:

1. A measuring system for automatically determining and/or monitoring a quality of a liquid or viscous foodstuff, comprising:

a housing with an interior space for at least one product container for the foodstuff, the product container having a product space for the foodstuff, and a lid with a probe having a thermometer which projects into the product space, a heating system for heating the interior space and a cooling system for cooling the interior space, a sensor device for determining a non-temperature quality-related parameter value of the foodstuff and a control unit which is operatively connected to the heating system and cooling system, the thermometer, and the sensor device, and is configured to:

control the measuring system, repeatedly measure the quality-related parameter value by means of the sensor device, store, process and/or export the measured quality-related parameter values, and control the heating system and/or the cooling system according to a desired time-temperature program for the interior space, wherein the cooling system comprises a cold buffer, a cooler for the cold buffer, and a separate refrigerant circuit, wherein the cold buffer comprises a buffer holder with a phase-transition material, wherein the refrigerant circuit comprises a closed-circuit line which is filled with a liquid refrigerant and is in heat-exchanging contact with the interior space and with the cold buffer, as well as a pump for pumping the refrigerant around, and wherein the control unit is configured to control the pump to make the refrigerant flow past and alongside the buffer holder and subsequently past the interior space with the product container, wherein the desired time-temperature program comprises inputted desired (1) one or more temperatures and (2) associated time periods and/or a number of repetitions in the control unit.

2. The measuring system according claim 1, wherein the cooling system comprises a Peltier heat pump which is configured to cool the buffer holder with phase-transition material.

3. The measuring system according to claim 1, wherein the time-temperature program comprises the control unit bringing the interior space to a temperature by means of the heating and cooling systems during a desired time period.

4. The measuring system according to claim 1, wherein the buffer holder comprises a heat-conducting foam, which is at least partly filled with the phase change material.

5. The measuring system according to claim 1, wherein the phase change material has a phase transition temperature below 0° C.

6. The measuring system according to claim 1, wherein the sensor device comprises at least one of the following:

a camera placed under the product container and directed upwards towards the product container, wherein the product container is at least partly transparent or open, a viscosity-measuring device for measuring the viscosity of the foodstuff, a measuring device for measuring electrical properties of the foodstuff, and an optical measuring device for measuring a transmission, a diffusion and/or a reflection value of said foodstuff.

7. The measuring system according to claim 1, wherein the measuring system comprises a plurality of housings, each provided with a container for the liquid or viscous foodstuff, wherein the plurality of housings are mechanically and electrically couplable to each other.

8. The measuring system according to claim 6, wherein the measuring device for measuring electrical properties of the foodstuff measures the conductivity of the foodstuff.

9. The measuring system according to claim 1, wherein the time-temperature program comprises the control unit bringing the interior space to a time dependent temperature by means of the heating and cooling systems during a desired time period.

10. The measuring system according to claim 1, wherein the control unit is configured to control the pump to make the refrigerant flow past the buffer holder and subsequently through the interior space with the product container.

11. The measuring system according to claim 4, wherein the heat-conducting foam is a metal foam.

12. The measuring system according to claim 11, wherein the metal foam is an aluminum foam.

13. The measuring system according to claim 1, wherein the cold buffer is configured to cool the refrigerant.

14. The measuring system according to claim 1, wherein the time-temperature program simulates a shelf life of the foodstuff.

15. The measuring system according to claim 1, wherein the time-temperature program simulates distribution and/or transportation of the foodstuff.

16. The measuring system according to claim 1, wherein the time-temperature program simulates cooled production and transportation of the foodstuff.

17. The measuring system according to claim 1, wherein the time-temperature program simulates non-refrigerated transportation of the foodstuff.

18. The measuring system according to claim 1, wherein the time-temperature program simulates use of the foodstuff outside of the product container.

19. The measuring system according to claim 1, wherein the time-temperature program subjects the foodstuff to cycles of warming up and cooling down.

20. The measuring system according to claim 1, wherein the time-temperature program comprises a period of subjecting the foodstuff to a heating temperature of from 30 to 130° C. and a period of subjecting the foodstuff to a cooling temperature of from 4 to 10° C.

21. The measuring system according to claim 1, wherein the desired time-temperature program comprises inputted desired (1) more than one non-overlapping temperature and (2) different time periods associated with each inputted desired temperature.

\* \* \* \* \*